(12) United States Patent
Miller et al.

(10) Patent No.: US 10,757,795 B2
(45) Date of Patent: Aug. 25, 2020

(54) DEVICE FOR DETERMINING SPATIALLY DEPENDENT X-RAY FLUX DEGRADATION AND PHOTON SPECTRAL CHANGE

(71) Applicant: KONINKLIJKE PHILIPS N.V., Eindhoven (NL)

(72) Inventors: Lester Donald Miller, Highland Heights, OH (US); Carolina Ribbing, Aachen (DE); Dionys Van De Ven, Hamburg (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 126 days.

(21) Appl. No.: 15/765,511

(22) PCT Filed: Oct. 4, 2016

(86) PCT No.: PCT/IB2016/055924
§ 371 (c)(1),
(2) Date: Apr. 3, 2018

(87) PCT Pub. No.: WO2017/060814
PCT Pub. Date: Apr. 13, 2017

(65) Prior Publication Data
US 2018/0279457 A1    Sep. 27, 2018

Related U.S. Application Data

(60) Provisional application No. 62/237,727, filed on Oct. 6, 2015.

(51) Int. Cl.
*H05G 1/26* (2006.01)
*A61B 6/00* (2006.01)
(Continued)

(52) U.S. Cl.
CPC ............. *H05G 1/26* (2013.01); *A61B 6/032* (2013.01); *A61B 6/4021* (2013.01); *A61B 6/586* (2013.01); *G01T 1/36* (2013.01); *H05G 1/54* (2013.01)

(58) Field of Classification Search
CPC ... H05G 1/26; H05G 1/54; G01T 1/36; A61B 6/586; A61B 6/4021; A61B 6/032
(Continued)

(56) References Cited

U.S. PATENT DOCUMENTS 4,497,062 A * 1/1985 Mistretta ............ G21K 1/10
378/158
5,568,531 A * 10/1996 Nishihagi ............ G01N 23/20
378/71
(Continued)

FOREIGN PATENT DOCUMENTS

WO    2015032664 A1    3/2015

OTHER PUBLICATIONS

Buzug, Thorsten M. "Computed Tomography", Springer-Verlag Berlin Heidelberg, 2008. pp. 31-48.
(Continued)

*Primary Examiner* — David P Porta
*Assistant Examiner* — Gisselle M Gutierrez
(74) *Attorney, Agent, or Firm* — Larry Liberchuk

(57) ABSTRACT

The invention relates to a device (10) for determining spatially dependent x-ray flux degradation and photon spectral change, a system (1) for determining spatially dependent x-ray flux degradation and photon spectral change for an x-ray tube (20), a method for spatially dependent x-ray flux degradation and photon spectral change for an x-ray tube (20), a computer program element for controlling such device (10) or system (1) for performing such method and a computer readable medium having stored such computer
(Continued)

program element. The device (10) for determining spatially dependent x-ray flux degradation and photon spectral change comprises an acquisition unit (11), a processing unit (12), a calculation unit (13), and a combination unit (14). The acquisition unit (11) is configured to acquire x-ray flux degradation data for the x-ray tube (20). The processing unit (12) is configured to process the x-ray flux degradation data into spatially dependent flux degradation data. The calculation unit (13) is configured to calculate at least a photon spectral change of the x-ray tube (20) and to convert the photon spectral change into a spatially dependent spectrum. The combination unit (14) is configured to combine the spatially dependent flux degradation data and the spatially dependent spectrum.

14 Claims, 2 Drawing Sheets

(51) Int. Cl.
    *H05G 1/54*     (2006.01)
    *A61B 6/03*     (2006.01)
    *G01T 1/36*     (2006.01)

(58) Field of Classification Search
    USPC .......................................................... 378/207
    See application file for complete search history.

(56) References Cited

U.S. PATENT DOCUMENTS

| | | | | |
|---|---|---|---|---|
| 5,668,850 | A | | 9/1997 | Abdel-Malek |
| 5,680,431 | A | * | 10/1997 | Pietras, III ............ H01J 35/065 |
| | | | | 378/119 |
| 6,118,125 | A | * | 9/2000 | Carlson .................... H05G 1/64 |
| | | | | 250/385.1 |
| 6,414,317 | B1 | * | 7/2002 | Francke .................. H01J 47/04 |
| | | | | 250/374 |
| 6,476,397 | B1 | * | 11/2002 | Francke .................. G01T 1/185 |
| | | | | 250/374 |
| 6,518,578 | B1 | * | 2/2003 | Francke .................. G01T 1/185 |
| | | | | 250/374 |
| 6,731,065 | B1 | * | 5/2004 | Francke .................. G01T 1/185 |
| | | | | 313/103 R |
| 7,302,041 | B2 | | 11/2007 | Deuringer |
| 7,959,343 | B2 | * | 6/2011 | Ijzerman ................ G02B 6/004 |
| | | | | 362/625 |
| 8,331,529 | B2 | | 12/2012 | Miller |
| 8,958,530 | B2 | | 2/2015 | Behling |
| 9,316,383 | B2 | * | 4/2016 | Ter Weeme ........ H05B 33/0821 |
| 2002/0001363 | A1 | * | 1/2002 | Kondo .................... B82Y 10/00 |
| | | | | 378/84 |
| 2003/0202546 | A1 | * | 10/2003 | Hartemann ......... G03F 7/70008 |
| | | | | 372/5 |
| 2013/0223594 | A1 | | 8/2013 | Sprong |
| 2014/0177810 | A1 | | 6/2014 | Gao |
| 2014/0270452 | A1 | * | 9/2014 | Goshen ................. G06T 3/4053 |
| | | | | 382/131 |

OTHER PUBLICATIONS

Mehranian, A. et al Quantitative Assessment of the Effect of Anode Surface Roughness on Diagnostic X-Ray Spectra: A Monte Carlo Simulation Study, 2009 IEEE Nuclear Science Symposium Conference Record, pp. 2902-2907.
Nema XR-29-2013 Standard Attributes on CT Equipment Related to Dose Optimization and Management, 2013.

\* cited by examiner

DEVICE FOR DETERMINING SPATIALLY DEPENDENT X-RAY FLUX DEGRADATION AND PHOTON SPECTRAL CHANGE

CROSS-REFERENCE TO PRIOR APPLICATIONS

This application is the U.S. National Phase application under 35 U.S.C. § 371 of International Application No. PCT/IB2016/055924, filed on Oct. 4, 2016, which claims the benefit of U.S. Provisional Patent Application No. 62/237,727, filed on Oct. 6, 2015. These applications are hereby incorporated by reference herein.

FIELD OF THE INVENTION

The invention relates to a device for determining spatially dependent x-ray flux degradation and photon spectral change, a system for determining spatially dependent x-ray flux degradation and photon spectral change for an x-ray tube, a method for spatially dependent x-ray flux degradation and photon spectral change for an x-ray tube, a computer program element for controlling such device or system for performing such method and a computer readable medium having stored such computer program element.

BACKGROUND OF THE INVENTION

Computed tomography (CT) systems comprise an x-ray tube that emits radiation that traverses an examination region and an x-ray detector that detects the radiation. The x-ray detector generates a signal indicative of the detected radiation, and the signal is reconstructed to generate volumetric image data indicative of the examination region.

The x-ray tube comprises a cathode and an anode. The cathode has included a filament that provides electrons that are accelerated towards and strike a target region on an anode under relatively high voltage. The interaction of the electrons with the anode material at the target region produces radiation that is emitted from the target region. The target region has been referred to as the focal spot. A collimator has been used to collimate the emitted radiation so that a radiation beam traverses the examination region.

U.S. Pat. No. 8,331,529 B2 discloses a medical imaging system with an x-ray source having a focal spot that emits radiation that traverses an examination region. The position of the focal spot along a longitudinal direction is a function of a temperature of one or more x-ray source components. The system further includes a detector that detects the radiation and a collimator disposed between the x-ray source and the examination region that collimates that radiation along the longitudinal direction. A focal spot position estimator dynamically computes an estimated position of the focal spot along the longitudinal direction based on the temperature of one or more x-ray source components. A collimator positioner positions the collimator along the longitudinal direction based on the estimated focal spot position prior to performing a scan.

It is well known that an x-ray output of the x-ray source or tube will decrease with usage. This is caused by thermal stress on the anode creating a roughened surface of an x-ray emitting area of the anode. The anode roughness in particular results from increased anode self-filtration as well as from excessive scattering of x-rays away from an exit window. However, thermal stress and temperatures are not uniform across the x-ray emitting area.

The decrease of x-ray output of the x-ray source is therefore a function of the history of temperature and time of the focal spot and the focal track as well as the physical mechanical properties of the anode. This is further complicated by the fact that in the x-ray tube there exist multiple focal spot sizes as well as dynamic focal spot switching. So the track wear depends on the separate history of focal spot size usage and the dynamic switching used. The x-ray output will also depend on the x-ray spot size used as well as the dynamic switch mode.

SUMMARY OF THE INVENTION

Hence, there may be a need to provide a device for determining spatially dependent x-ray flux degradation and photon spectral change through life of an x-ray tube.

The problem of the present invention is solved by the subject-matters of the independent claims, wherein further embodiments are incorporated in the dependent claims. It should be noted that the aspects of the invention described in the following apply also to the device for determining spatially dependent x-ray flux degradation and photon spectral change, the system for determining spatially dependent x-ray flux degradation and photon spectral change, the method for spatially dependent x-ray flux degradation and photon spectral change, the computer program element, and the computer readable medium.

According to the present invention, a device for determining spatially dependent x-ray flux degradation and photon spectral change is presented. The device for determining spatially dependent x-ray flux degradation and photon spectral change comprises an acquisition unit, a processing unit, a calculation unit, and a combination unit.

The acquisition unit is configured to acquire x-ray flux degradation data for the x-ray tube. The processing unit is configured to process the x-ray flux degradation data into spatially dependent flux degradation data. The calculation unit is configured to calculate at least a photon spectral change of the x-ray tube and to convert the photon spectral change into a spatially dependent spectrum. The combination unit is configured to combine the spatially dependent flux degradation data and the spatially dependent spectrum.

The combination may be an estimation or prediction of a spectral content of an x-ray beam generated through life of an x-ray tube based on spatial dependant track wear. Therefore, the device for determining spatially dependent x-ray flux degradation and photon spectral change can be used to provide (real-time) information on dose reduction and spectral hardening. Such information is highly valuable for (remote) tube monitoring, pro-active service models and spectral image quality compliance. Also more accurate dose control in the x-ray systems can be achieved.

The combination of spatially dependent flux degradation data and spatially dependent spectrum may be a combination or composition of non-homogeneous data into single effective value(s). The single effective value(s) may be a single representative for dose and a single representative for spectrum or a single representative for both dose and spectrum.

In an example, the combination unit is configured to predict a spectral content of an x-ray beam generated by the x-ray tube based on the combination of spatially dependent flux degradation data and the spatially dependent spectrum. Thereby and as will be shown in detail in the following, the combination unit is enabled to predict a the spatially dependent spectrum or photon energy distribution of an x-ray beam as a function of tube usage history as well as dynamic switching pattern used for the x-ray exposure. The prediction is possible in case of a single use focal spot that is not switching by calculating the amount of x-ray output degradation and then estimating the spectral change due to an equivalent filtration of the beam of target material. The prediction is also possible in case different focal spot wear tracks overlap as the focal spot can be dynamically moved during scanning to increase the sampling rate of the data acquisition. In the latter case, spectral changes are estimated based on combinations of different wear areas.

The x-ray flux degradation data may be simulated or measured. In an example, the acquisition unit is configured to acquire x-ray flux degradation data by measuring an output of the x-ray tube. The output of the x-ray tube may be measured and fed back to a prediction calculation algorithm to learn and then provide an improved prediction. In an example, the measuring of the output of the x-ray tube is based on at least one of the group of a scanner detector signal, a scanner reference detector signal, a scanner detector noise variance, a scanner reference detector noise variance, an x-ray system detector signal, an x-ray system reference detector signal, an x-ray system detector noise variance, an x-ray system reference detector noise variance, a spectral detector dual energy or photon counting, at least two reference detectors with different filtering properties, back scattered electrons, x-ray scattering in an anode of the x-ray tube, comparing detector signals for different focal spots and/or focal spot sizes over time and combinations thereof.

With increasing dose awareness, measuring the output of the x-ray tube or tube monitoring for complying with image quality requirements may become increasingly important. Monitoring spectral output of the x-ray tube may be used for newer imaging techniques employing energy resolving detectors (e.g. photon counting). In this way, spectral hardening which would otherwise cause image artifacts can be compensated for.

The x-ray flux degradation data may be processed into spatially dependent flux degradation data by spatially dependent flux degradation data based on usage history data or by measuring the spatially dependent flux degradation data by means of a focused x-ray mapping beam or by measuring an x-ray dose drop based on detector noise, backscattered electrons and/or the like. These options are explained in the following in detail.

In an example, the processing unit is configured to process the x-ray flux degradation data into spatially dependent flux degradation data by calculating spatially dependent flux degradation data based on usage history data. In an example, the simulation or calculation of the spatially dependent flux degradation data based on usage history data is a function of a temperature of the focal spot, a temperature of the focal track, a time, a switching mode of the x-ray tube and a characterizing number for a size and a radial position of the focal spot. Usage history data may comprise a history of focal spot size usage and dynamic switching, which can be assessed by logging or monitoring settings of the x-ray tube during tube life. Such settings may be saved in log files of the x-ray tube or an imaging system.

In other words, the x-ray flux degradation data or dose degradation can be calculated for any given x-ray exposure. The factors of importance are the time, the temperature of the track as a function of time, the focal spot temperature as a function of time, and the dynamic focal spot switching pattern (diagonal, quad etc.). Furthermore, each focal spot position is important because the radius position can be different in the case of certain focal spot patterns. Therefore, for use in an x-ray degradation equation, each focal spot size and position can be enumerated by a number "n". So each focal spot size and radial position will get a unique number. Exemplarily:

n=1 Small focal spot in the dynamic x-deflection position
n=2 Large focal spot in the dynamic x-deflection position
n=3 Large focal spot in the dynamic diagonal position inner radial position
n=4 Large focal spot in the dynamic diagonal position outer radial position
n=5 Small focal spot in the dynamic quad position in the inner radial position
n=6 Small focal spot in the dynamic quad position in the outer radial position For a focal spot "n" and an x-ray exposure "j", x-ray flux degradation data or a dose drop "Δdrop" can be calculated by $$\Delta drop_{n,j} = \int f(TT(t,n,\text{mode}), TF(t,n,\text{mode})) dt$$

wherein
t=time
TT=temperature of the track
TF=temperature of the focal spot
mode=the switch mode i.e. diagonal, quad etc.

In an example, the processing unit is further configured to calculate cumulative flux degradation data as a function of a sum of focal spots, a sum of x-ray exposures by the x-ray tube, the spatially dependent flux degradation data and a weighing factor based on the characterizing number for a size and a radial position of the focal spot and a type of x-ray scan. In other words, the cumulative flux degradation data or cumulative dose drop for a certain type of scan "m" can be computed as $$drop_m = \sum_{n=1}^{numFocal} \sum_{j=1}^{numExposures} W_{n,m} \cdot \Delta drop_{n,j}$$

wherein
W=weighing factor where a scanning position or focal spot overlaps portions of other tracks or focal spots In an example, the acquisition unit is configured to adapt the simulation based on the spatially dependent flux degradation data. In reality, an actual output can diverge from a calculated output so it is advantageous to provide feedback for a correction to a simulation algorithm. This can be done in a number of ways. The first being a direct reset of a total dose drop and then continuing calculations from there and the second being to provide an update of the algorithm parameters. Other ways for this might include neuro-networks, linear regression, logistic regression or other learning algorithms.

In another example, the processing unit is configured to process the x-ray flux degradation data into spatially dependent flux degradation data by measuring the spatially dependent flux degradation data by means of a focused x-ray mapping beam. The measurement by means of a focused x-ray mapping beam may comprise a deflection of the focused x-ray mapping beam to different radial positions along a focal track of the x-ray tube and a measuring and mapping of local flux degradation data based on the different radial positions along the focal track. In other words, to achieve a determination of a spatial distribution of dose degradation by making a dedicated measurement, a focal spot size is to be adjusted or selected to be as small as possible. Then, the x-ray beam is deflected to different radial positions along the track and a dose profile can be mapped by measuring an x-ray tube output as a function of position. With this information, spatially dependent flux degradation data can be calculated for any focal spot size and switching mode.

In another example, it is possible to use this measurement by means of a focused x-ray mapping beam to move a focal spot to a different location on the focal track that e.g. does not have so much wear. Practically, a small focal spot can be moved e.g. to an outer track region where less degradation takes place. For better images, a system reconstruction can then be told by an x-ray system where a new location is.

In another example, the processing unit is configured to process the x-ray flux degradation data into spatially dependent flux degradation by measuring an x-ray dose drop based on detector noise and/or backscattered electrons. The measuring may be done by the acquisition unit. The electrons that may be normally scattered of the x-ray target may have different trajectories due to the changes of the target that cause the x-ray degradation in the first place. Some of these may get collected in other parts of the x-ray tube such as an insert frame or scattered electron trap. These currents can be measured to indirectly infer an amount of dose degradation of an x-ray beam.

In an example, the calculation unit is configured to calculate at least a photon spectral change of the x-ray tube and to convert the photon spectral change into the spatially dependent spectrum based on x-ray radiation intensity, x-ray radiation energy, an attenuation coefficient and a distance travelled by x-ray radiation in an attenuation medium.

The spatially dependent spectrum can be approximated from the fact that a dose drop is a function of increased x-ray scatter and self-absorption in an anode. For a certain amount of dose drop, there will be a scattering factor and a self-absorption factor which are both functions of the radiation energy. A total attenuation can be modeled using Lambert-Beers law with a target material to estimate the spatially dependent spectrum or spectral distribution:

$$I(s) = \int_0^{E_{max}} I_0(E) e^{\int_0^s \mu(E,x)dx} dE$$

wherein

I=radiation intensity

E=radiation energy $\mu$=total linear attenuation coefficient (sum of absorption and scatter coefficients)

s=distance travelled by the radiation in the attenuating medium, wherein at the current energies (50-120 keV) and high Z, photoelectric absorption may dominate the total attenuation.

The spatially dependent photon spectrum can be approximated or even predicted for a given uniform attenuation. Superposition can be added up to the total effect since attenuations are not uniform across the track. The spatially dependent photon spectra can then be a weighted average of the constituent parts. For instance, if a focal spot is riding on a track area where half of the dose drop is 20% and half is 10%, then the actual attenuation might be about 15%. In this case, the spatially dependent photon spectra obtained from the 10% can be averaged with the spatially dependent photon spectra obtained from the 20% to provide resultant spatially dependent photon spectra.

Exemplarily, the combination unit is further configured to directly map the actual and/or the predicted spectrum and intensity of an x-ray beam generated by the x-ray tube as a function of the radial position along the focal spot track area. With increasing dose awareness and use of photon counting detection, monitoring of tube dose and spectral degradation will become indispensable.

According to the present invention, also a system for determining spatially dependent x-ray flux degradation and photon spectral change for an x-ray tube is presented. The system for determining spatially dependent x-ray flux degradation and photon spectral change for an x-ray tube comprises a the x-ray tube and a device for determining spatially dependent x-ray flux degradation and photon spectral change as described above. The x-ray tube is configured to provide an x-ray beam used by the device for determining spatially dependent x-ray flux degradation and photon spectral change for the x-ray tube.

According to the present invention, also a method for spatially dependent x-ray flux degradation and photon spectral change for an x-ray tube is presented. It comprises the following steps, not necessarily in this order:

a) acquiring x-ray flux degradation data for the x-ray tube;

b) processing the x-ray flux degradation data into spatially dependent flux degradation data;

c) calculating at least a photon spectral change of the x-ray tube and converting the photon spectral change into a spatially dependent spectrum; and d) combining the spatially dependent flux degradation data and the spatially dependent spectrum.

According to the present invention, also a computer program element is presented, wherein the computer program element comprises program code means for causing the system as defined in the independent claim to carry out the steps of the method as defined in the independent claim when the computer program is run on a computer controlling the system.

It shall be understood that the device for spatially dependent x-ray flux degradation and photon spectral change for an x-ray tube, the system, method, the computer program element for controlling such device and the computer readable medium having stored such computer program element according to the independent claims have similar and/or identical preferred embodiments, in particular, as defined in the dependent claims. It shall be understood further that a preferred embodiment of the invention can also be any combination of the dependent claims with the respective independent claim.

These and other aspects of the present invention will become apparent from and be elucidated with reference to the embodiments described hereinafter.

BRIEF DESCRIPTION OF THE DRAWINGS

Exemplary embodiments of the invention will be described in the following with reference to the accompanying drawings.

DETAILED DESCRIPTION OF EMBODIMENTS

Figure 1:
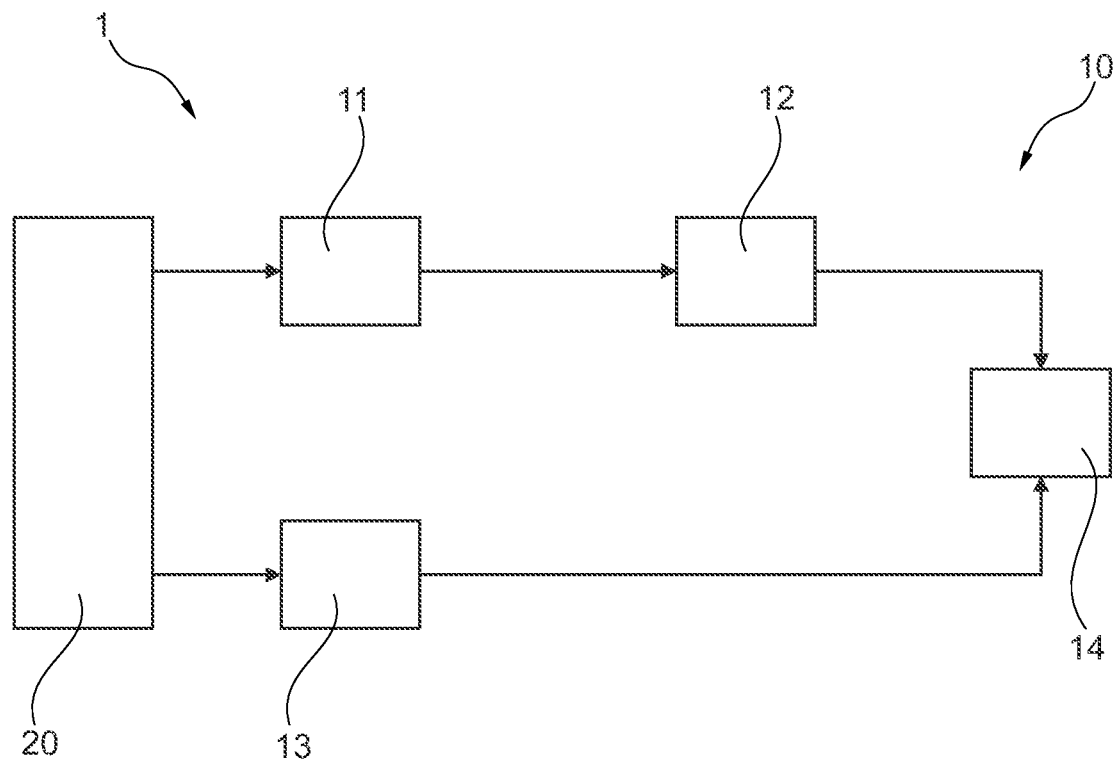
FIG. 1 shows a schematic drawing of an example of a system and a device for determining spatially dependent x-ray flux degradation and photon spectral change for an x-ray tube according to the invention.

FIG. 1 shows schematically and exemplarily an embodiment of a system 1 for determining spatially dependent x-ray flux degradation and photon spectral change for an x-ray tube 20 according to the invention. The system 1 comprises the x-ray tube 20 and a device 10 for determining spatially dependent x-ray flux degradation and photon spectral change. The x-ray tube 20 provides an x-ray beam used by the device 10 for determining spatially dependent x-ray flux degradation and photon spectral change for the x-ray tube 20.

The device 10 for determining spatially dependent x-ray flux degradation and photon spectral change comprises an acquisition unit 11, a processing unit 12, a calculation unit 13 and a combination unit 14.

The acquisition unit 11 acquires x-ray flux degradation data for the x-ray tube 20. The x-ray flux degradation data may be acquired by simulation or by measuring an output of the x-ray tube 20.

The processing unit 12 processes the x-ray flux degradation data into spatially dependent flux degradation data. The processing into spatially dependent flux degradation data may be done by calculation based on usage history, measurement by using a focused x-ray mapping beam or measurement of an x-ray dose drop based on detector noise, backscattered electrons and/or the like.

The calculation unit 13 calculates at least a photon spectral change of the x-ray tube 20 and converts or calculates the photon spectral change into a spatially dependent spectrum based on x-ray radiation intensity, x-ray radiation energy, an attenuation coefficient and/or a distance travelled by x-ray radiation in an attenuation medium. The spatially dependent photon spectra can then be a weighted average of the constituent parts.

The combination unit 14 combines the spatially dependent flux degradation data and the spatially dependent spectrum. The combination may be an estimation or prediction of a spectral content of an x-ray beam generated through life of an x-ray tube 20 based on spatial dependant track wear. The combination of spatially dependent flux degradation data and spatially dependent spectrum may be a combination or composition of non-homogeneous data into single effective value(s).

The output of the x-ray tube 20 may be measured and fed back to a prediction calculation algorithm to learn and provide an improved prediction.

The x-ray flux degradation data or the dose drop "Δdrop" may be acquired by a simulation based on a calculation depending on a focal spot "n", an x-ray exposure "j", time "t", temperature of the track "TT", temperature of the focal spot "TF" and switch mode i.e. diagonal, quad etc. "mode":

$$\Delta drop_{n,j} = \int f(TT(t,n,\text{mode}), TF(t,n,\text{mode})) dt$$

The simulation or calculation may be adapted based on the spatially dependent flux degradation data.

Figure 2:
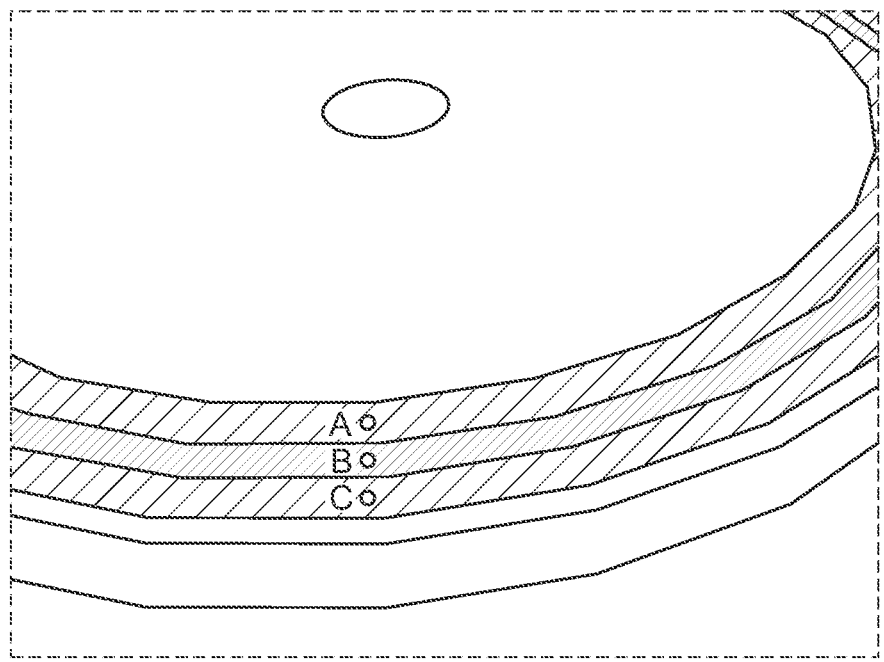
FIG. 2 shows schematically and exemplarily a measuring of a spatially dependent flux degradation data by means of a focused x-ray mapping beam.

A measuring of the spatially dependent flux degradation data by means of a focused x-ray mapping beam is shown in FIG. 2. This measurement by means of a focused x-ray mapping beam comprises a deflection of a focused x-ray mapping beam to different radial positions A, B, C along a focal track of the x-ray tube 20 and a measuring and mapping of local flux degradation data based on the different radial positions A, B, C along the focal track. In other words, to achieve a determination of a spatial distribution of dose degradation by making a dedicated measurement, a focal spot size is to be adjusted or selected to be as small as possible. Then, the x-ray beam is deflected to different radial positions A, B, C along the track and a dose profile can be mapped by measuring an x-ray tube 20 output as a function of position. With this information, spatially dependent flux degradation data can be calculated for any focal spot size and switching mode.

Figure 3:
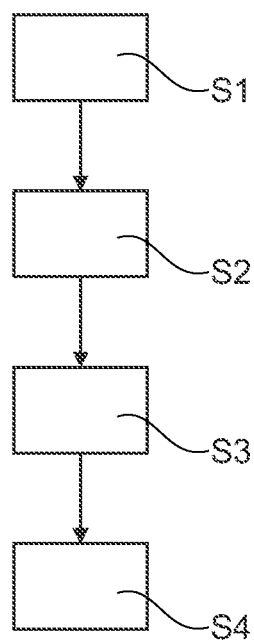
FIG. 3 shows basic steps of an example of method for spatially dependent x-ray flux degradation and photon spectral change for an x-ray tube according to the invention.

FIG. 3 shows a schematic overview of steps of a method for spatially dependent x-ray flux degradation and photon spectral change for an x-ray tube 20. The method comprises the following steps, not necessarily in this order:

In a first step S1, acquiring x-ray flux degradation data for the x-ray tube 20.

In a second step S2, processing the x-ray flux degradation data into spatially dependent flux degradation data.

In a third step S3, calculating at least a photon spectral change of the x-ray tube 20 and converting the photon spectral change into a spatially dependent spectrum.

In a fourth step S4, combining the spatially dependent flux degradation data and the spatially dependent spectrum.

Other configurations to use the method for spatially dependent x-ray flux degradation and photon spectral change for an x-ray tube 20 according to the invention are as follows:

Configuration 1
Simulate dose drop
Use the dose drop to correct a statistical model, e.g. a de-noising model Configuration 2
Simulate dose drop
Use the dose drop to predict a spectral content of an x-ray beam for spectral CT imaging, including photon counting Configuration 3
Simulate dose drop
Use measurement feedback to correct a simulation model (e.g. detector noise variance method, back scattered electron measurement)
Use the dose drop to correct a statistical model Configuration 4
Simulate dose drop
Use measurement feedback to correct a simulation model
Use the dose drop to predict a spectral content of an x-ray beam Configuration 5
Directly measure spatially dependant anode dose degradation
Update simulation model if used
Use the dose drop to correct a statistical model Configuration 6
Directly measure a spatially dependant anode dose degradation
Update the simulation model if used
Use the dose drop to predict a spectral content of the x-ray beam In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfil the procedure of an exemplary embodiment of the method as described above.

According to a further exemplary embodiment of the present invention, a computer readable medium, such as a CD-ROM, is presented wherein the computer readable medium has a computer program element stored on it, which computer program element is described by the preceding section.

A computer program may be stored and/or distributed on a suitable medium, such as an optical storage medium or a solid state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfil the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A device for determining spatially dependent x-ray flux degradation and photon spectral change for an x-ray tube, comprising:
processor circuitry configured to:
acquire x-ray flux degradation data for the x-ray tube;
process the x-ray flux degradation data into spatially dependent flux degradation data by calculating spatially dependent flux degradation data based on usage history data, wherein the calculation of the spatially dependent flux degradation data based on usage history data is a characterizing number for a size and a radial position of the focal spot;
calculate at least a photon spectral change of the x-ray tube and to convert the photon spectral change into a spatially dependent spectrum; and
combine the spatially dependent flux degradation data and the spatially dependent spectrum.

2. The device according to claim 1, wherein the processor circuitry is further configured to predict a spectral content of an x-ray beam generated by the x-ray tube based on the combination of spatially dependent flux degradation data and the spatially dependent spectrum.

3. The device according to claim 1, wherein the processor circuitry is configured to acquire x-ray flux degradation data by measuring an output of the x-ray tube.

4. The device according to claim 3, wherein the measuring of the output of the x-ray tube is based on at least one of the group of a scanner detector signal, a scanner reference detector signal, a scanner detector noise variance, a scanner reference detector noise variance, an x-ray system detector signal, an x-ray system reference detector signal, an x-ray system detector noise variance, an x-ray system reference detector noise variance, a spectral detector dual energy or photon counting, at least two reference detectors with different filtering properties, back scattered electrons, x-ray scattering in an anode of the x-ray tube, comparing detector signals for different focal spots and/or focal spot sizes over time and combinations thereof.

5. The device according to claim 1, wherein the calculation of the spatially dependent flux degradation data based on usage history data further comprises at least one of the group of a function of a temperature of the focal spot, a temperature of the focal track, a time, and a switching mode of the x-ray tube.

6. The device according to claim 5, wherein the processor circuitry is further configured to calculate cumulative flux degradation data as a function of a sum of focal spots, a sum of x-ray exposures by the x-ray tube, the spatially dependent flux degradation data and a weighing factor based on the characterizing number for a size and a radial position of the focal spot and a type of x-ray scan.

7. The device according to claim 1, wherein the processor circuitry is configured to process the x-ray flux degradation data into spatially dependent flux degradation data by measuring the spatially dependent flux degradation data by means of a focused x-ray mapping beam.

8. The device according to claim 7, wherein the measurement by means of a focused x-ray mapping beam is used to move a focal spot to a different location on a focal track.

9. The device according to claim 1, wherein the processor circuitry is configured to process the x-ray flux degradation data into spatially dependent flux degradation by measuring an x-ray dose drop based on detector noise and/or backscattered electrons.

10. The device according to claim 9, wherein the processor circuitry is configured to calculate at least a photon spectral change of the x-ray tube and to convert the photon spectral change into the spatially dependent spectrum based on an x-ray radiation intensity, an x-ray radiation energy, an attenuation coefficient and a distance traveled by x-ray radiation in an attenuation medium.

11. The device according to claim 10, wherein the calculation of the processor circuitry is adapted based on the spatially dependent flux degradation data.

12. A system for determining spatially dependent x-ray flux degradation and photon spectral change for an x-ray tube, comprising:
the x-ray tube, and
a device for determining spatially dependent x-ray flux degradation and photon spectral change, comprising processor circuitry configured to:
acquire x-ray flux degradation data for the x-ray tube;
process the x-ray flux degradation data into spatially dependent flux degradation data by calculating spatially dependent flux degradation data based on usage history data, wherein the calculation of the spatially dependent flux degradation data based on usage history data is a characterizing number for a size and a radial position of the focal spot;
calculate at least a photon spectral change of the x-ray tube and to convert the photon spectral change into a spatially dependent spectrum; and
combine the spatially dependent flux degradation data and the spatially dependent spectrum,
wherein the x-ray tube is configured to provide an x-ray beam used by the device for determining spatially dependent x-ray flux degradation and photon spectrum change for the x-ray tube.

13. A method for spatially dependent x-ray flux degradation and photon spectral change for an x-ray tube, comprising:
acquiring x-ray flux degradation data for the x-ray tube;
processing the x-ray flux degradation data into spatially dependent flux degradation data by calculating spatially dependent flux degradation data based on usage history data, wherein the calculation of the spatially dependent flux degradation data based on usage history data is a characterizing number for a size and a radial position of the focal spot;
calculating at least a photon spectral change of the x-ray tube and converting the photon spectral change into a spatially dependent spectrum; and
combining the spatially dependent flux degradation data and the spatially dependent spectrum.

14. A non-transitory computer readable medium having stored a computer program element for controlling a device or system, which, when being executed by processor circuitry, is adapted to perform the method of claim 13.

\* \* \* \* \*